United States Patent [19]
Dobak, III et al.

[11] Patent Number: 6,151,901
[45] Date of Patent: *Nov. 28, 2000

[54] MINIATURE MIXED GAS REFRIGERATION SYSTEM

[75] Inventors: John D. Dobak, III, San Diego, Calif.; Ray Radebaugh; Marcia L. Huber, both of Louisville, Colo.; Eric D. Marquardt, Lakewood, Colo.

[73] Assignees: CryoGen, Inc., San Diego, Calif.; The United States of America as represented by the Secretary of Commerce, Washington, D.C.

[*] Notice: Under 35 U.S.C. 154(b), the term of this patent shall be extended for 494 days.

[21] Appl. No.: 08/542,123

[22] Filed: Oct. 12, 1995

[51] Int. Cl.[7] .................................................. F25B 19/02
[52] U.S. Cl. ............................ 62/51.2; 62/293; 606/23; 606/24
[58] Field of Search ........................ 62/51.2, 293, 29.3; 606/23, 24

[56] References Cited

U.S. PATENT DOCUMENTS

| | | |
|---|---|---|
| 3,272,203 | 9/1966 | Chato . |
| 3,273,356 | 9/1966 | Hoffman .................................. 62/51.2 |
| 3,298,371 | 1/1967 | Lee ........................................ 62/293 X |
| 3,398,738 | 8/1968 | Lamb et al. . |
| 3,401,533 | 9/1968 | Maybury .................................. 62/51.2 |
| 3,431,750 | 3/1969 | Lefranc .................................... 62/51.2 |
| 3,439,680 | 4/1969 | Thomas, Jr. . |
| 3,477,434 | 11/1969 | Hood, Jr. et al. . |
| 3,536,075 | 10/1970 | Thomas, Jr. et al. . |
| 3,662,755 | 5/1972 | Rautenbach et al. . |
| 3,913,581 | 10/1975 | Ritson et al. . |
| 4,015,606 | 4/1977 | Mitchiner et al. .................... 62/293 X |
| 4,207,897 | 6/1980 | Lloyd et al. . |

(List continued on next page.)

FOREIGN PATENT DOCUMENTS

| | | | |
|---|---|---|---|
| 2477406 | 9/1981 | France | ..................................... 606/23 |
| 0839516 | 6/1981 | U.S.S.R. | .................................. 606/23 |
| 1774140 | 11/1992 | U.S.S.R. | ................................... 62/51.2 |
| 1 336 892 | 11/1973 | United Kingdom . | |
| 2080117 | 2/1982 | United Kingdom | ..................... 606/23 |

OTHER PUBLICATIONS

Hubbell, Richard H.; *New Heat Transfer and Friction Factor Design Data for Perforated Plate Heat Exchangers*; pp. 383–390; 1988; Advanced Cryogenic Engineering, vol. 33.

Jichuan, Hu; *Heat Transfer Characteristics of a Perforated Plate: Part II—Heat Transfer Coefficients for the Separate Working Surfaces*; pp. 318–322; Sep., 1990; Cryogenics, vol. 30.

Khatri, Ajay; *A Throttle Cycle Refrigerator Operating Below 77K*; 8 pages; date and place of publication unknown.

Venkatarathnam, G.; *Heat Transfer and Flow Friction Correlations in Perforated Plate Matrix Heat Exchangers*; pp. 313–317; Sep., 1990; Cryogenics, vol. 30.

(List continued on next page.)

*Primary Examiner*—Ronald Capossela
*Attorney, Agent, or Firm*—Gerald W. Spinks

[57] ABSTRACT

A miniature mixed gas refrigeration system is disclosed, having a coaxial catheter with an inner high pressure supply lumen and an outer low pressure return lumen. The gas mixture is pressurized by a compressor to a pressure less than 420 psia, for safety reasons. The distal portion of the outer lumen contains a micro-miniature heat exchanger constructed of laminated plates or sheets. The plates or sheets establish high pressure and low pressure passageways, with high surface area, having a tortuous path for the gas flow to maximize heat exchange. The high pressure outlet of the heat exchanger is connected to a Joule-Thomson expansion element where the high pressure gas is expanded isenthalpically to a lower temperature at least as low as 180K. This low temperature gas cools a heat transfer element mounted in the outer wall of the catheter, to cool an external object. Return gas flows back through the heat exchanger to pre-cool the incoming high pressure gas mixture.

7 Claims, 6 Drawing Sheets

U.S. PATENT DOCUMENTS

| | | |
|---|---|---|
| 4,377,168 | 3/1983 | Rzasa et al. . |
| 4,781,033 | 11/1988 | Steyert et al. ............................ 62/51.2 |
| 4,829,785 | 5/1989 | Hersey ................................ 62/51.2 X |
| 5,078,713 | 1/1992 | Varney . |
| 5,101,894 | 4/1992 | Hendricks ............................ 62/51.2 X |
| 5,139,496 | 8/1992 | Hed .......................................... 606/23 |
| 5,147,355 | 9/1992 | Friedman et al. . |
| 5,275,595 | 1/1994 | Dobak, III . |
| 5,281,212 | 1/1994 | Savage et al. . |
| 5,281,213 | 1/1994 | Milder et al. . |
| 5,281,215 | 1/1994 | Milder . |
| 5,281,217 | 1/1994 | Edwards et al. . |
| 5,324,286 | 6/1994 | Fowle . |
| 5,337,572 | 8/1994 | Longsworth . |
| 5,365,750 | 11/1994 | Greenthal ............................. 62/51.2 X |
| 5,423,807 | 6/1995 | Milder . |
| 5,595,065 | 1/1997 | Boiarski et al. ..................... 62/51.2 X |

OTHER PUBLICATIONS

Venkatarathnam, G.; *Matrix Heat Exchangers and Their Application in Cryogenics Systems*; pp. 907–918; Nov., 1990; Cryogenics, vol. 30.

First list of abstracts related to perforated plate heat exchangers, compiled for the applicant through a computer data base search; list not published.

Second list of abstracts related to perforated plate heat exchangers, compiled for the applicant through a computer data base search; list not published.

Coxeter, Ruth; *Developments to Watch—The Deep Freeze for Irregular Heartbeats*; p. 90; Sep. 19, 1994; Business Week.

Gage, Andrew A.; *Current Progress in Cryosurgery*; pp. 483–486; Mar. 28, 1988; American College of Cryosurgery, 8th Annual Meeting.

Little, W. A.; *Advances in Joule—Thomson Cooling*; pp. 1–10; date unknown; place of publication unknown.

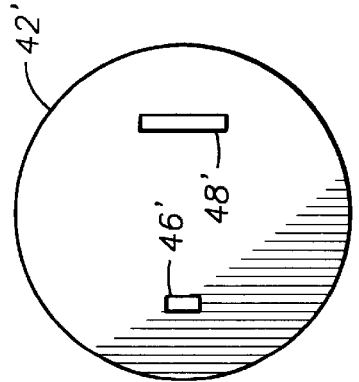
FIG. 9
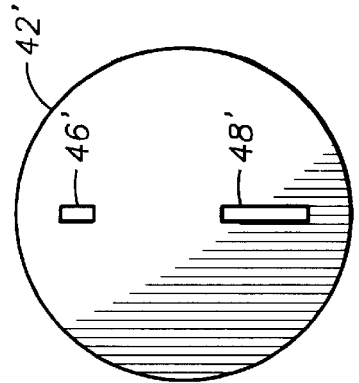
FIG. 8
FIG. 7
FIG. 6
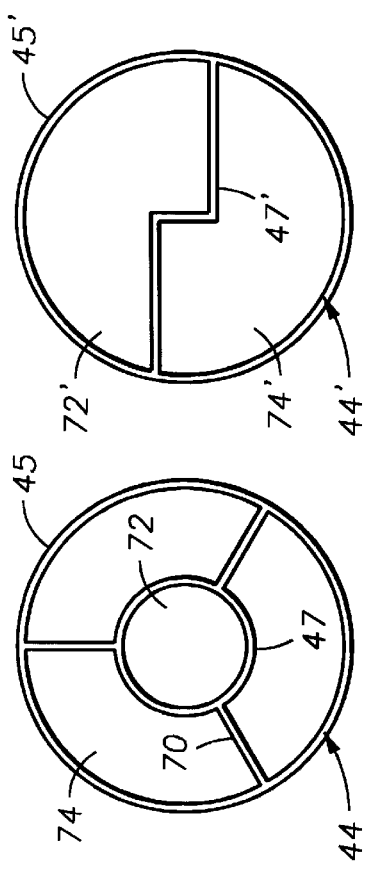
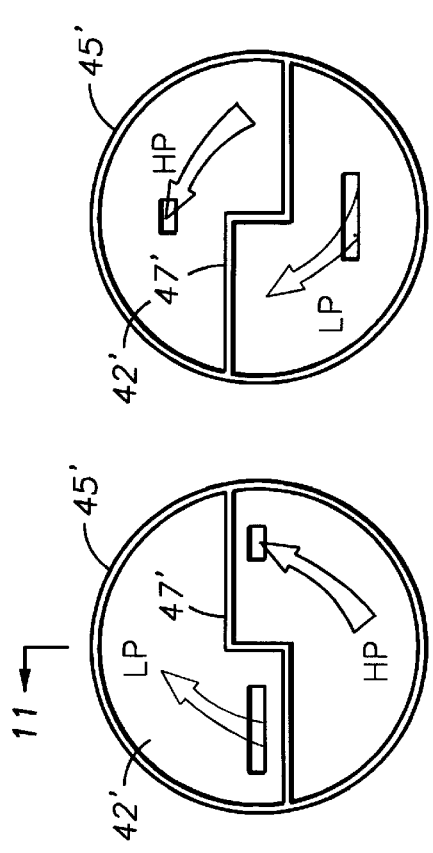
FIG. 10

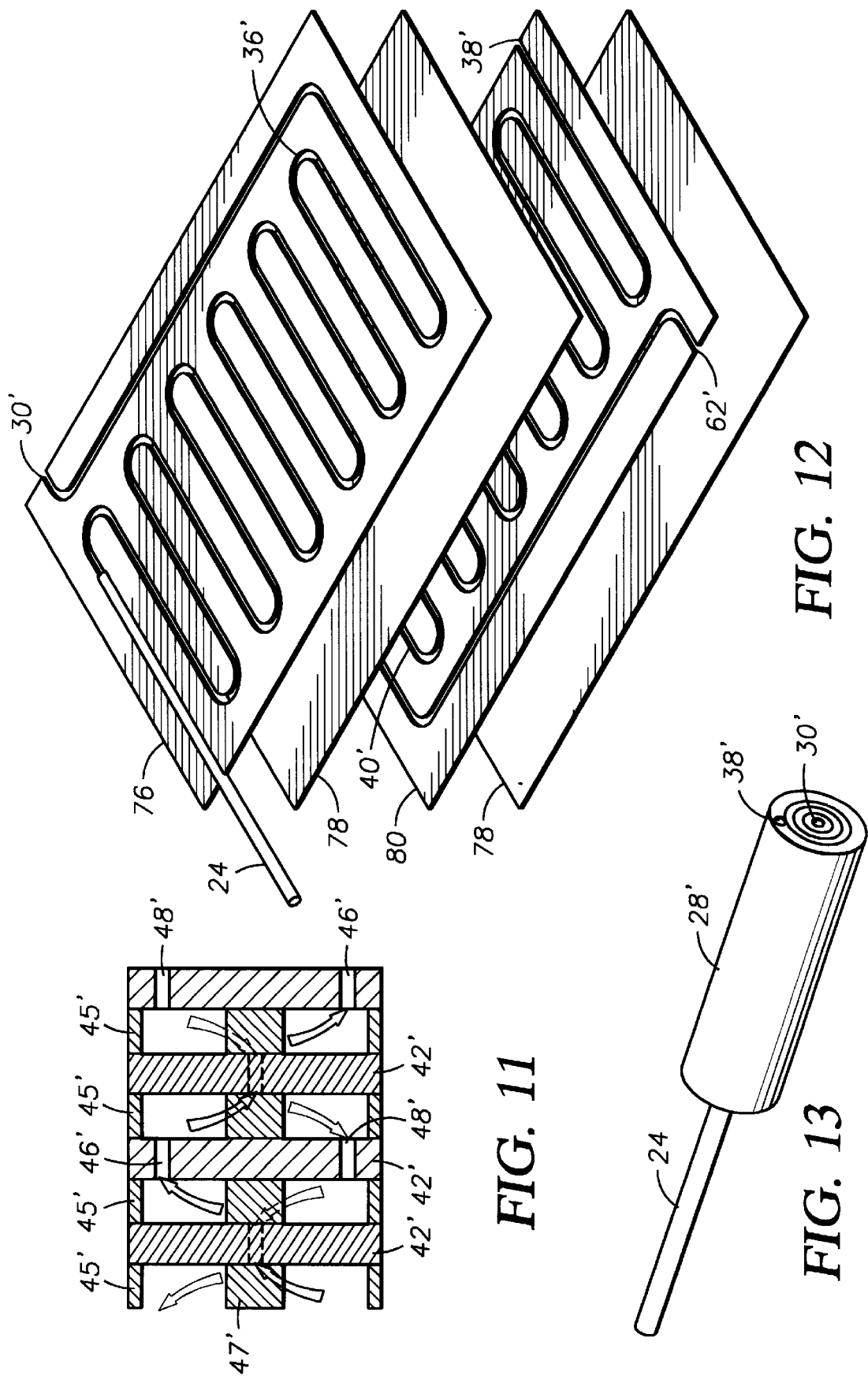

MINIATURE MIXED GAS REFRIGERATION SYSTEM

GOVERNMENT LICENSE RIGHTS

The U.S. Government has a paid up license in this invention and the right to have this invention practiced on behalf of the Government, as provided for by the terms of Contract No. CRADA: CN-1090, awarded by the National Institute of Standards and Technology.

FIELD OF INVENTION

This invention is in the field of apparatus used to cool miniature objects or very small portions of objects to very low temperatures. The objects to be cooled may include biological matter, electronic components, and others.

BACKGROUND OF THE INVENTION

In many different fields of endeavor, it is desirable to be able to selectively cool a very small or even microscopic object to a very low temperature without affecting the temperature of surrounding objects. This is true in the field of electronics, where it may be desirable to apply cooling to a miniature component on a circuit board without substantially cooling adjacent components. It is also true in the field of medicine, where it may be desirable to be able to cool miniature discrete portions of biological tissue to very low temperatures in the performance of cryosurgery, without substantially cooling adjacent tissues of the organ. In the interest of simplicity, this specification will address the fulfillment of this need in the field of medicine, but it should be understood that application of the present invention in other fields, such as electronics, is also contemplated within the scope of the present invention.

Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems are not optimally designed to have sufficient precision and flexibility to allow their widespread use endoscopically and percutaneously.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe or other applicator used in a given application is therefore designed with the optimum shape and size for the application, to achieve this selective freezing of tissue. Where a probe is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe at the location of the tissue to be frozen, without having any undesirable effect on other organs or systems.

Currently known cryosurgical systems typically use liquid nitrogen or nitrous oxide as coolant fluids. Liquid nitrogen is usually either sprayed onto the tissue to be destroyed, or it is circulated to cool a probe which is applied to the tissue. Liquid nitrogen has an extremely low temperature of approximately 77K, and a high cooling capacity, making it very desirable for this purpose. However, liquid nitrogen typically evaporates and escapes to the atmosphere during use, requiring the continual replacement of storage tanks. Further, since the liquid is so cold, the probes and other equipment used for its application require vacuum jackets or other types of insulation. This makes the probes relatively complex, bulky, and rigid, and therefore unsuitable for endoscopic or intravascular use. The need for relatively bulky supply hoses and the progressive cooling of all the related components make the liquid nitrogen instruments less than comfortable for the physician, as well, and they can cause undesired tissue damage.

A nitrous oxide system typically achieves cooling by pressurizing the gas and then expanding it through a Joule-Thomson expansion element, such as a valve, orifice, or other type of flow constriction, at the end of a probe tip. Any such device will be referred to hereinafter simply as a Joule-Thompson "expansion element". The typical nitrous oxide system pressurizes the gas to 700 to 800 psia., to reach practical temperatures of no lower than about 190K to 210K. Nitrous oxide systems are not able to approach the temperature and power achieved by the nitrogen systems. The maximum temperature drop that can be achieved in a nitrous oxide system is to 184K, which is the boiling point of nitrous oxide. The nitrous oxide system does have some advantages, in that the inlet high pressure gas is essentially at room temperature until it reaches the Joule-Thomson element at the probe tip. This eliminates the need for insulation of the system, facilitating miniaturization and flexibility to some extent. However, because of the relatively warm temperatures and low power, tissue destruction and other applications are limited. For many such applications, temperatures below 184K are desirable. Further, the nitrous oxide must typically be vented to atmosphere after passing through the system, since affordable compressors suitable for achieving the high pressures required are not reliable and readily commercially available.

In most Joule-Thomson systems, single non-ideal gasses are pressurized and then expanded through a throttling component or expansion element, to produce isenthalpic cooling. The characteristics of the gas used, such a boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity. Finned tube heat exchangers have been used, but these are necessarily bulky to achieve the required cooling, preventing their use in micro-miniature systems such as catheter delivered instruments. Smaller heat exchangers have also been known, constructed of photo-etched glass plates. These heat exchange systems are still in the range of several centimeters square in size, making them still too bulky for true micro-miniature use, such as in endoscopes, catheters, and other systems. Further, these heat exchangers are planar and difficult to incorporate into tubular structures such as catheters or endoscopes. In many of these medical applications, the dimensions of the components must be less than approximately 3 mm. in width to allow incorporation into through a catheter or endoscope, and preferably less than 15 mm. in length to allow sufficient flexibility.

Heat exchanger requirements can be reduced somewhat by pre-cooling the gases prior to the probe tip heat exchanger. This can be done by incorporating a Peltier device in the flow path prior to the probe tip heat exchanger. Gas flowing through a heat exchanger on the surface of the cold side of the Peltier device would be cooled prior to reaching the probe tip heat exchanger. Alternatively, the inlet high pressure stream could be split so that a portion of the stream could be diverted and expanded to cool the remaining portion of the inlet stream prior to reaching the probe tip heat exchanger.

A dramatic improvement in cooling in Joule-Thomson systems can be realized by using a mixture of gasses rather than a single gas. For example, the addition of hydrocarbons to nitrogen can increase the cooling power and temperature drop for a given inlet pressure. Further, it is possible to reduce the pressure and attain performance comparable to the single gas system at high pressure. Similar to single gas systems, these mixed gas systems have heat exchanger requirements and are limited in their miniaturization potential by the size of the heat exchanger. The improvement in cooling performance realized by mixed gas systems is very desirable for medical and other microminiature systems.

Some mixed gas systems have been designed where high pressure is not a major concern, and where bulky high efficiency heat exchangers can be used, but they are typically used in defense and aerospace applications The glass plate heat exchangers mentioned above are used in some such systems, and these systems sometimes require pressures of 1200 psia. In many applications, such as laser systems, superconductors, electronics and cryosurgery, pressures above approximately 420 psia. are undesirable for safety reasons, and because the devices exhibit poor longevity, high cost, and poor reliability. Further, endoscopic or percutaneous use prevents implementation of any heat exchanger having a width of greater than about 3 mm. or a length of more than about 15 mm.

Specifically, it would be desirable to develop a long, slender, flexible cryoprobe, such as a transvascular cardiac catheter. Cardiac catheters must be very slender, in the range of less than 5 mm., and they must exhibit considerable flexibility, in order to be inserted from an access point in a remote blood vessel into the heart. A cryosurgical catheter to be used in such an application must also have a relatively low operating pressure for safety reasons. It must have the cooling capacity to overcome the ambient heat load imposed by the circulating blood, yet it must be able to achieve a sufficiently low temperature to destroy the target tissue. Finally, the cold heat transfer element must be limited to the tip or end region of the catheter, in order to prevent the damaging of tissue other than the target tissue.

It is an object of the present invention to provide a miniature mixed gas refrigeration system which is capable of achieving a cooling temperature of 184K or less, utilizing a high pressure of no greater than 420 psia., with components capable of fitting within a miniature delivery system such as a transvascular cardiac catheter. It is a further object of the present invention to provide a miniature refrigeration system utilizing a micro-miniature heat exchanger to provide a sufficiently cool high pressure gas mixture for isenthalpic expansion through a Joule-Thomson expansion element, to achieve an expanded gas temperature of at least as low as 183K, to have sufficient cooling power to maintain this temperature when a heat load is applied, and to perform with an inlet high pressure of no greater than 420 psia.

SUMMARY OF THE INVENTION

The present invention comprises a miniature refrigeration system having a compressor for compressing a gas mixture to a pressure up to 420 psia. The high pressure gas mixture from the compressor is fed into a high pressure supply tube, such as in inner tube of a cardiac catheter, which in turn feeds the high pressure gas mixture into the inlet port at the proximal end of a cylindrical micro-miniature counterflow heat exchanger. The high pressure gas mixture passes through a high pressure supply passageway within the heat exchanger and exits through a port at the distal end of the heat exchanger. The high pressure distal port is connected to the inlet of a Joule-Thomson expansion element, in which the gas mixture is isenthalpically expanded to a lower pressure and a temperature at least as low as 183K. The expansion element can have a second stage in which the gas mixture is further expanded isothermally to absorb additional heat from the surroundings.

The gas mixture escaping from the Joule-Thomson expansion element is exposed to the inner surface of a heat transfer element mounted in the wall of an outer tube coaxial with the inner tube. The expanded gas mixture cools the heat transfer element to a temperature of at least as low as 180K and then returns through the low pressure return passageway of the heat exchanger. This cools the high pressure gas from its original ambient temperature to a lower temperature. From the low pressure outlet of the heat exchanger, the expanded gas mixture flows into the lumen of the outer tube, outside the inner high pressure tube, to return to the compressor.

The heat exchanger can have a laminated construction of several different types. In a preferred embodiment, the heat exchanger is constructed of a plurality of plates and spacers stacked alternatingly along the axial dimension of the heat exchanger. The plates have a first plurality of holes establishing the high pressure passageway of the heat exchanger, and a second plurality of holes establishing the low pressure passageway of the heat exchanger. The high pressure holes are segregated from the low pressure holes. Spacers with larger openings are stacked between the plates to promote turbulent flow and insure effective heat exchange. The plates and spacers can be fastened together by a process such as diffusion bonding.

The Joule-Thomson expansion element can be a sintered metal plug made by sintering a plurality of metal beads into a metal cup, to provide the required pressure drop. The two different stages, if present, can utilize different sizes of beads, different cross sectional areas, and different packing densities. The heat transfer element can take the optimum shape for matching the object or tissue to be cooled. For example, a metal plug can be installed in the tip of the outer tube or catheter, for applying cooling through the extreme distal tip of the catheter. Alternatively, a relatively narrow metal strip can be mounted in a side wall of the catheter, near the distal tip, for applying cooling to a narrow strip of tissue.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 6 is an elevational view of a preferred embodiment of a spacer used in the micro-miniature heat exchanger used in the probe shown in FIG. 3;

FIG. 7 is an elevational view of a second embodiment of a spacer used in a second embodiment of the micro-miniature heat exchanger;

FIG. 8 is an elevational view of a first configuration of plate used in the second embodiment of the micro-miniature heat exchanger;

FIG. 9 is an elevational view of a second configuration of plate used in the second embodiment of the micro-miniature heat exchanger, showing the different orientation of high pressure and low pressure ports;

FIG. 10 is a series of elevational views of plates and spacers used in the second embodiment of the micro-miniature heat exchanger, showing the flow of supply and return gas mixtures;

FIG. 11 is a sectional view of the plurality of plates and spacers shown in FIG. 10, showing the flow of supply and return gas mixtures;

FIG. 12 is a perspective view of a third embodiment of the micro-miniature heat exchanger used in the present invention, prior to final shaping;

FIG. 13 is a perspective view of the heat exchanger shown in FIG. 12, after final shaping;

DESCRIPTION OF PREFERRED EMBODIMENTS

Figure 1:
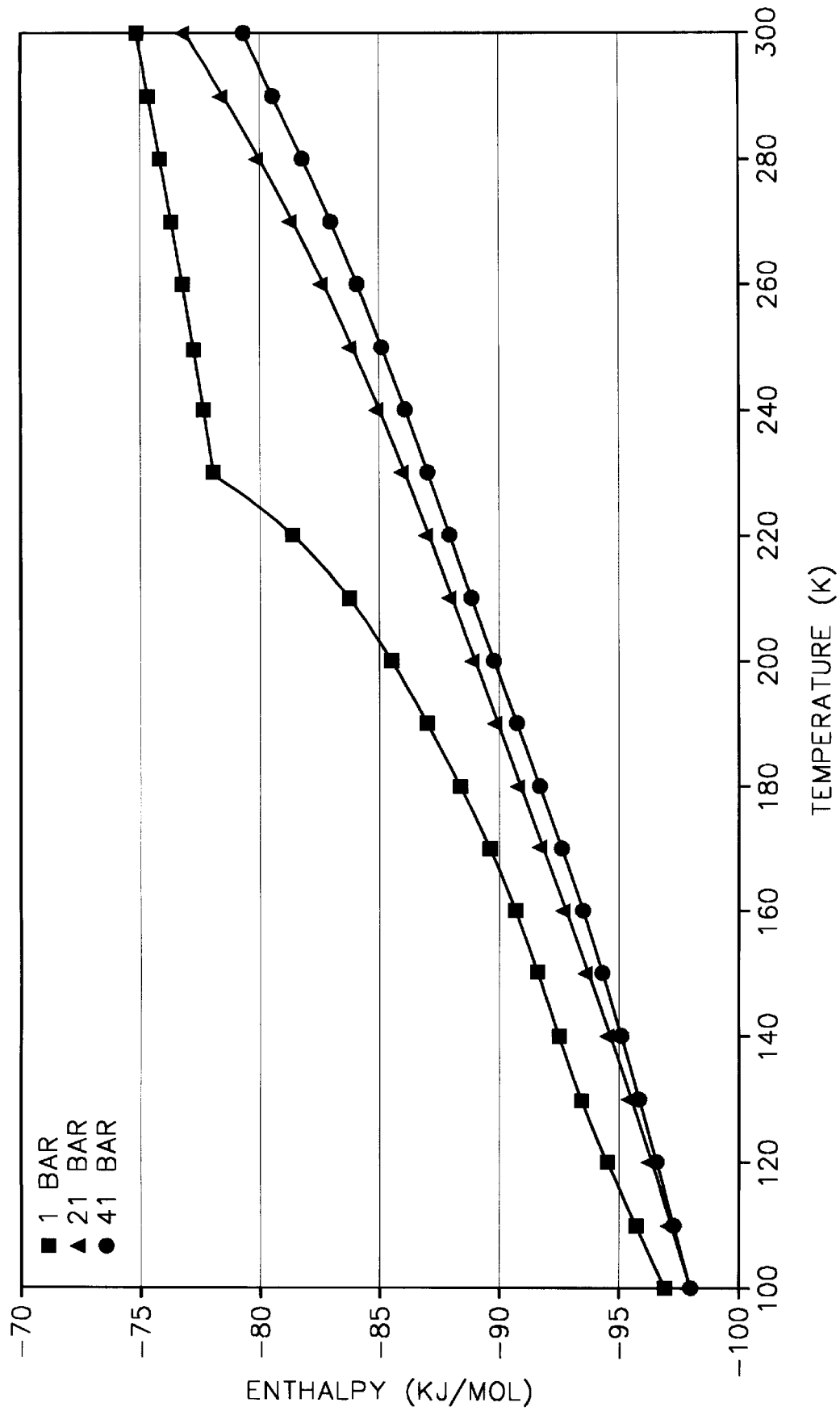
FIG. 1 is a graph of enthalpy vs. temperature for a selected gas mixture used with the present invention.

A key to the success of the present invention was in shifting from the use of a single gas to the use of a gas mixture, since no known single gasses are capable of achieving the necessary cooling capacity at the required temperatures, given the size limitations and pressure limitations imposed on systems intended for use in the selected applications. Several gas mixtures have been identified for use with the present invention, and it is anticipated that others will be identified as well. Appropriate gas mixtures may take various forms, and they may be either hydrocarbon-based or non-hydrocarbon-based. By way of example only, the mixture currently identified as the preferred mixture for many applications is 30 percent Methane, 23 percent Nitrogen, 23 percent Isobutane, 19 percent Ethane, and 5 percent Propane. The temperature capability of isenthalpic expansion of such a as mixture is illustrated by FIG. 1, which shows enthalpy curves for this gas mixture at pressures of 1 bar (14.5 psia.), 21 bar (305 psia.), and 41 bar (595 psia.). Isenthalpic expansion from one of the higher pressures to the lower pressure proceeds horizontally to the left across the graph, accompanied by a drop in temperature. The lowest temperature attainable would be at the point where the curves cross, somewhere below 100K. The lower the temperature of the high pressure gas mixture, the lower the temperature which can be achieved by the isenthalpic expansion through the Joule-Thomson expansion element. It can also be seen from the graph that there is little difference between the temperatures attainable by expanding from 41 bar and expanding from 21 bar. For example, assume that the heat exchanger used is capable of cooling the high pressure gas mixture to a temperature of 210 K, just upstream of the expansion element. If a high pressure of 21 bar is used, the isenthalpic expansion will result in a temperature of 180K. If the gas mixture is instead pressurized to 41 bar, the attainable temperature after isenthalpic expansion is still only about 173K. Further, the cooling capacity, or power, represented by the difference between the high pressure curve and the 1 bar curve at a given temperature is similar, whether the high pressure is 21 bar or 41 bar. Therefore, the added safety achieved by lowering the initial pressure to 21 bar, or approximately 300 psia, results in only a minor loss of performance. Obviously, for a given gas mixture, the more efficient the heat exchanger, the lower the probe temperature that can ultimately be obtained, and the greater will be the cooling power.

Figure 2:
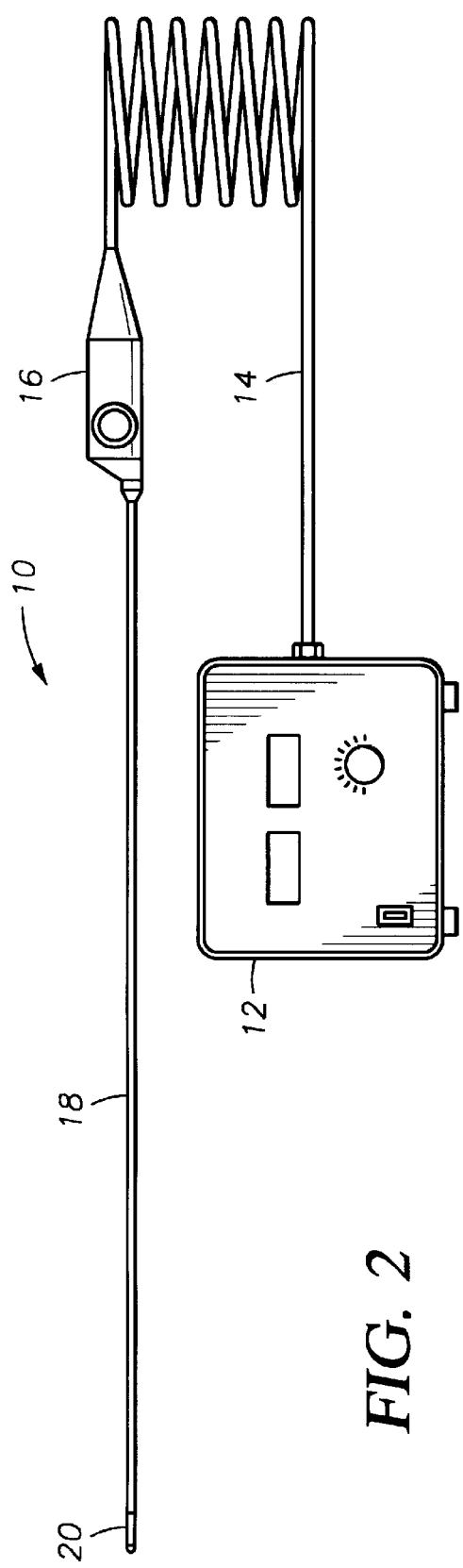
FIG. 2 perspective view of one embodiment of the miniature refrigeration system of the present invention.

FIG. 2 shows a refrigeration system 10 according to the present invention, for a cryosurgical application. The system 10 consists of a commercially available single stage compressor 12, a flexible dual lumen hose 14 connected to the inlet and outlet of the compressor 12, a steering handle 16, and a cryosurgical probe 18. The compressor 12 can be any of several oil based compressors available, typically using an aftercooler, an oil separator, and an adsorption filter. Alternatively, an oil free compressor could also be utilized. The hose 14 can be any flexible dual lumen hose suitable for the pressures and chemical exposures involved, for the gas mixture used. The handle 16 can have a control expansion element installed, for the physician to use in throttling the flow rate of the gas mixture. Alternatively, the flow could be controlled via a foot switch that regulates flow at the compressor. The probe 18 is a coaxial catheter having an inner tube for conducting the high pressure gas mixture from the outlet of the compressor 12 and for returning the expanded low pressure gas to the inlet of the compressor 12. The probe 18 has a distal end portion or region 20 in which the heat exchanger, expansion element, and heat transfer element are located. The probe 18 is of suitable diameter, length, and flexibility to be inserted to the object to be cooled, such as through the vascular system of a patient into the heart.

Figure 3:
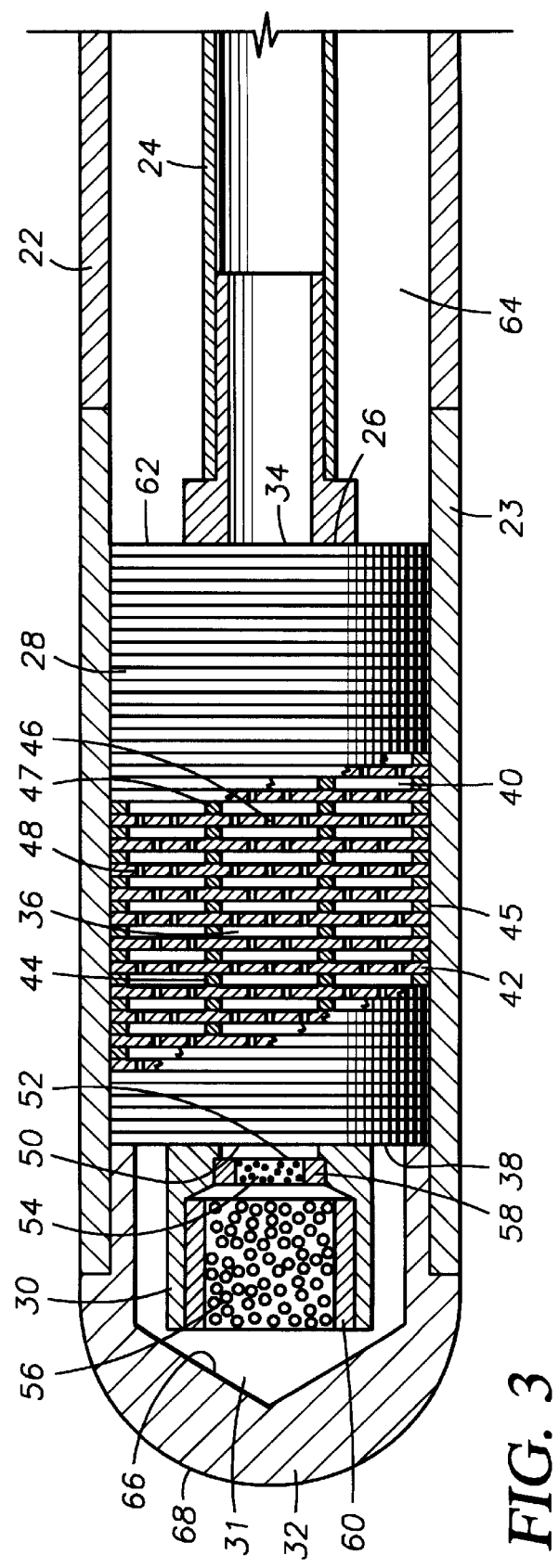
FIG. 3 is a partial section view of the distal end portion of the cryosurgical probe portion of the refrigeration system shown in FIG. 2.

FIG. 3 shows a partial section view of the distal end portion 20 of the coaxial catheter 18. The catheter 18 consists of an outer tube 22 and an inner tube 24. The outer tube 22 can be continuous to the end of the catheter 18, or it can have an extension 23, which should be considered for all practical purposes an integral part of the outer tube 22. The outer tube 22 is made according to known methods from a wire-braided polymer, such as a polyamide-ether copolymer. The inner tube 24 is made from a wire-braided polyimide having a pressure capability sufficient for the maximum high pressure anticipated for the particular application. The inner tube 24 is connected by means of an inlet fitting 26 to the proximal end of a micro-miniature heat exchanger 28. Mounted to the distal end of the heat exchanger 28 is a Joule-Thomson expansion element 30. The distal end of the expansion element 30 is exposed to a cavity 31 at the distal end of the outer tube 22 or extension 23, closed by a heat transfer element 32. The expanded gas mixture cools the inner surface 66 of the heat transfer element 32, thereby cooling the outer surface 68. The outer surface 68 is placed against the object to be cooled by the physician.

More specifically, the distal end of the inner high pressure tube 24 is connected by means of the inlet fitting 26 to the high pressure inlet port 34 at the proximal end of the heat exchanger 28. This high pressure inlet port 34 leads to a high pressure supply passageway 36 through the heat exchanger, shown as the central axial portion of the heat exchanger 28 in this embodiment. The heat exchanger 28 also has a low pressure inlet port 38 at its distal end exposed to the cavity 31. This low pressure inlet port 38 leads to a low pressure return passageway 40, shown as the outer annular portion of the heat exchanger, surrounding the high pressure passageway 36. The low pressure, low temperature gas mixture flowing through the low pressure passageway pre-cools the high pressure, higher temperature gas mixture flowing through the high pressure passageway. The heat exchanger 28 is constructed of alternately stacked copper plates 42 and stainless steel spacers 44, diffusion bonded together. Other methods of attachment could be used without departing from the spirit of the present invention. The heat exchanger 28 is shown, for the sake of simplicity in this figure, as having an outer skin over the plates 42 and spacers 44, but in actuality, the skin is optimally provided by an outer ring 45 on each spacer 44 being bonded to the extreme outer annular portion of each plate 42, as will be made more clear below. The central portion of each plate 42 has a plurality of holes 46 therethrough, which along with central openings in the spacers 44 establish the high pressure passageway 36 longitudinally through the heat exchanger 28 in the distal direction. Similarly, the outer portion of each plate 42 has a plurality of holes 48 therethrough, which along with outer openings in the spacers 44 establish the low pressure passageway 40 longitudinally through the heat exchanger 28 in the proximal direction. The high pressure passageway 36 is separated from the low pressure passageway 40 by an inner ring 47 on each spacer 44.

High pressure gas mixture passing through the heat exchanger 28 exits the high pressure passageway at a high pressure outlet port 50 at the central distal portion of the heat exchanger to enter the inlet 52 of the Joule-Thomson isenthalpic expansion element 30. This expansion element 30 has a first stage 54 of a first diameter, in which isenthalpic expansion to a second larger diameter takes place, lowering the temperature of the gas mixture to the design temperature. The gas mixture then passes through the second stage 56 in which isothermal expansion takes place, leaving the gas mixture still at the desired temperature, but absorbing heat from the surrounding structure in the process. The first stage 54 is constructed by filling a metal cylinder 58 with a selected size of metal beads, at a selected packing density, to achieve the desired rate of expansion of the gas. The beads are sintered in place in the cylinder 58. Similarly, the second stage 56 is constructed by filling a second metal cylinder 60 with a selected size of metal beads, at a selected packing density, to achieve the desired rate of expansion of the gas. Typically, the beads in the second stage 56 will have a larger surface area to enhance heat transfer.

The expanded gas mixture which passes through the heat exchanger 28 in the proximal direction exits the annular low pressure passageway 40 at a low pressure outlet port 62 at the proximal end of the heat exchanger 28. This expanded gas mixture enters the inner lumen 64 of the outer tube 22, surrounding the inner tube 24, to be returned to the compressor 12.

Figure 5:
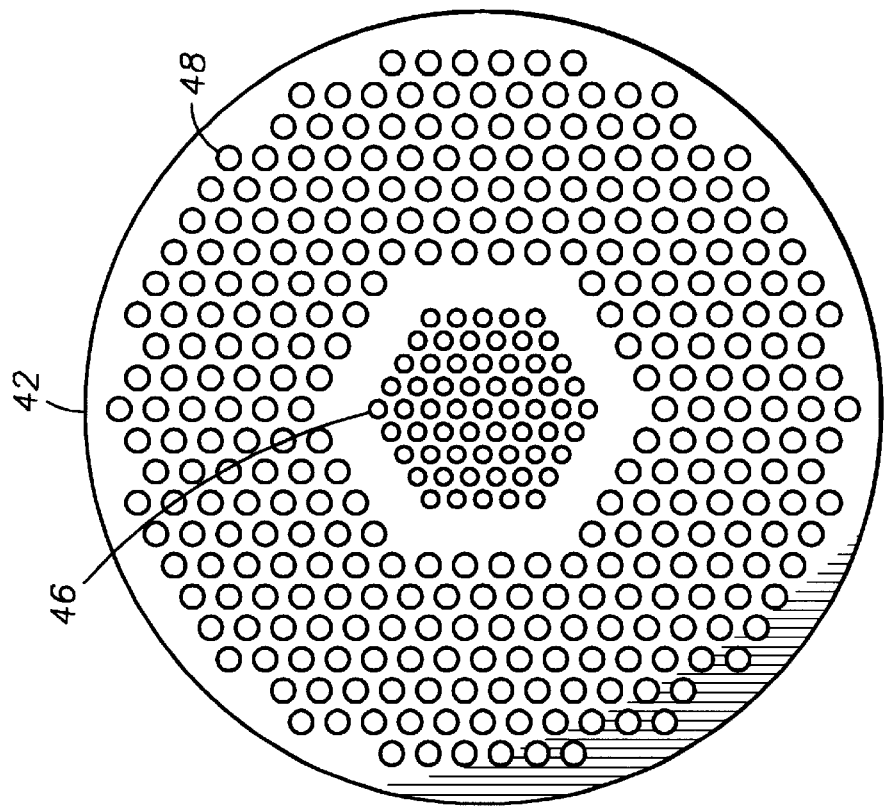
FIG. 5 is an elevational view of a second configuration of heat exchanger plate, showing a different angular orientation of holes from the orientation shown in FIG. 4.
Figure 4:
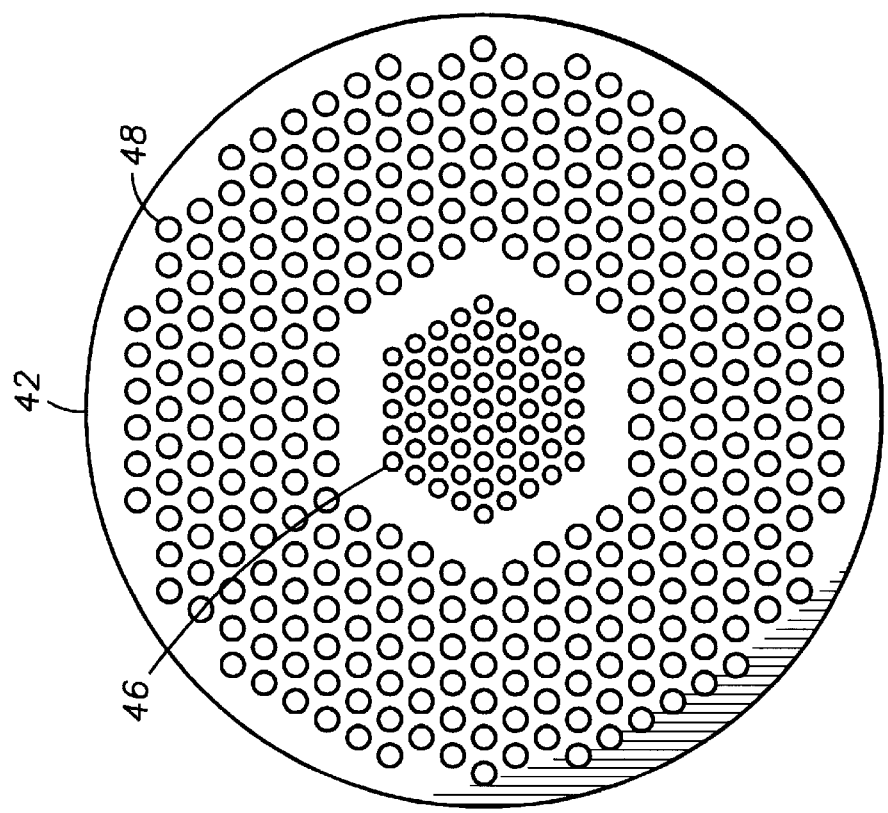
FIG. 4 is an elevational view of a preferred embodiment of one configuration of heat exchanger plate used in the micro-miniature heat exchanger utilized in the cryosurgical probe shown in FIG. 3.

FIGS. 4 and 5 more clearly illustrate the structure of the plates 42 and their angular orientation within the heat exchanger 28. Each plate 42 has a first plurality of high pressure holes 46 through its central portion, and a second plurality of low pressure holes 48 through its outer annular portion. Typically, the diameter and spacing of the inner holes 46 are smaller than the diameter and spacing of the outer holes 48. Selection of hole diameter and spacing for the two different passageways is designed for an optimization of minimum pressure drop and maximum heat transfer rate at the two different pressures, according to well known design principles. FIGS. 4 and 5 are also intended to show the relative angular orientation between adjacent plates 42. It can be seen that the two figures actually depict the same plate configuration, with the plate 42 in FIG. 5 simply being rotated relative to the plate 42 in FIG. 4. The hole pattern used in the plate 42 can be varied, with the objective being to maximize the heat exchange contact between the gas mixture and the plate 42. Gas does not flow from the high pressure portion of the plate to the low pressure portion, being prevented by contact between the plate 42 and the inner ring 47 of the interdisposed spacer 44, as shown earlier in FIG. 3. The relative angular orientation between adjacent plates 42 can also be varied according to the chosen hole pattern, with the objective being to maximize turbulence of the gas mixture, to promote heat transfer. It can be clearly seen from FIGS. 3, 4, and 5 that gas flowing through the heat exchanger 28 in either of the passageways 36, 40 follows a somewhat tortuous path, with a substantial portion of the flow path being involved in movement transverse to the axis of the heat exchanger 28. In the embodiment shown, the transverse component of the flow results from the relative angular orientation between adjacent plates 42. This tortuous path promotes efficient heat transfer, allowing the microminiature heat exchanger 28 to achieve the required temperature drop to enable the desired isenthalpic expansion through the Joule-Thomson flow restriction expansion element 30, ultimately producing the designed cooling temperature. Heat flow in this embodiment tends to be substantially radial.

FIG. 6 shows the preferred embodiment of the spacer 44, which is interspersed between the plates 42. The spacer 44 has an outer ring 45 and an inner ring 47 supported in the desired concentric relationship by spokes 70. An inner opening 72 within the inner ring 47 serves as a portion of the high pressure passageway 36 between plates 42. A plurality of outer openings 74 between the inner ring 47 and the outer ring 45 serve as a portion of the low pressure passageway 40 between plates 42. The inner ring 47 serves as a divider between the high and low pressure openings 72, 74.

FIG. 7 shows a second embodiment of the spacer 44' which can be used with a second embodiment of plates 42' shown in FIGS. 8 and 9. The spacer 44' has an outer ring 45' and a high/low pressure divider 47'. This divider 47' separates the high pressure opening 72' from the low pressure opening 74'. It can be seen that this spacer 44' can be turned over from the orientation shown in FIG. 7, to reverse the orientation of the divider 47', for reasons that will become apparent below. FIG. 8 shows a plate 42' having a relatively small rectangular high pressure hole 46' and a relatively large rectangular low pressure hole 48', with the long dimensions of the rectangular holes 46', 48' being vertically aligned. FIG. 9 shows the same type of plate 42', with the rectangular holes 46', 48' being arranged horizontally.

These two hole patterns and the two spacer orientation possible with the spacer 44' are used to create a series of adjacent plates 42' and spacers 44' as shown in FIG. 10.

FIG. 10 shows this series arranged from left to right as they would be arranged from the proximal end of the heat exchanger toward the low pressure end, in successive series. The HP arrows show the flow path of the high pressure gas mixture into the plane of the page, while the LP arrows show the path of the low pressure gas mixture out of the plane of the page. FIG. 11 further illustrates this flow path, by showing a vertical section through the stacked plates 42' and spacers 44'. Dashed lines are used to show the locations of hidden high and low pressure holes. Here again, it can be seen that the gas mixture follows a tortuous path through both the high pressure and low pressure passageways 36, 40, but in this embodiment, the transverse components of the flow are much more pronounced than in the first embodiment, and the heat flow tends to be more axial than radial.

FIGS. 12 and 13 show yet another embodiment of the heat exchanger of the present invention, constructed of rolled sheets, rather than stacked plates and spacers. The inner tube 24 of the catheter 18 is shown connected to a labyrinthian high pressure passageway 36' etched into a first sheet 76. A constriction is also etched into the outlet of the high pressure passageway 36', to form a Joule-Thomson expansion element 30'. A second sheet 80 has a low pressure passageway 40' etched therein, with an inlet 38' and an outlet 62'. Positioned in between the first sheet 76 and the second sheet 80 are spacer sheets 78 to separate the high pressure and low pressure passageways 36', 401. The sheets 76, 78, 80 can be laminated in the orientation shown and diffusion bonded together, or joined by some other suitable process. The assembly is then rolled as shown in FIG. 13, to construct a cylindrical heat exchanger 28'.

Figure 14:
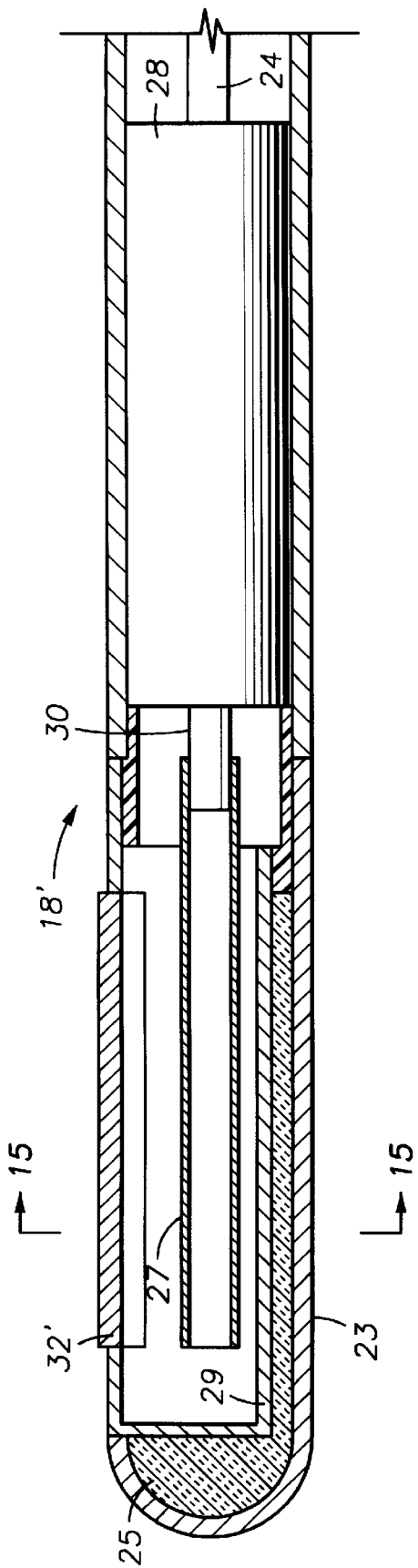
FIG. 14 is a partial section view of a second embodiment of the distal end portion of the cryosurgical probe used in the present invention, showing a narrow elongated heat transfer element.
Figure 15:
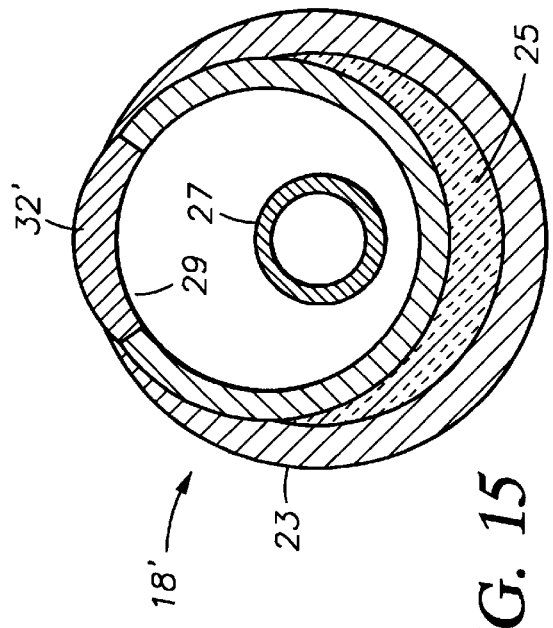
FIG. 15 is a section view of the second embodiment, taken along the line 15—15 in FIG. 14.

FIGS. 14 and 15 show a second embodiment of the distal end portion of the catheter 18', having a slender elongated heat transfer element 32'. This embodiment illustrates that the end portion of the catheter can have a fluid tube 27 affixed to the expansion element 30, a fluid chamber 29, and insulation 25 between the fluid chamber 29 and the extension tube 23. This construction insures that the cooling power is applied primarily through the heat transfer element 32'.

While the particular invention as herein shown and disclosed in detail is fully capable of fulfilling the objects previously stated, it is to be understood that this disclosure is merely an illustration of the presently preferred embodiments of the invention and that no limitations are intended other than those described in the appended claims.

We claim:

1. A miniature refrigeration system, comprising:

a compressor for pressurizing a gas mixture to a pressure of approximately 420 psia, said compressor having an inlet and an outlet;

a hollow elongated supply tube, said supply tube having a proximal end and a distal end, said proximal end of said supply tube being connectable to said outlet of said compressor;

a hollow elongated return tube disposable substantially coaxially over said supply tube, said return tube having a proximal end and a distal end, said proximal end of said return tube being connectable to said inlet of said compressor;

a laminated counterflow heat exchanger mounted within said return tube, adjacent to said distal end of said return tube, said heat exchanger having a high pressure passageway and a low pressure passageway, said high pressure passageway having at least one proximal port and at least one distal port, said at least one proximal port of said high pressure passageway being connected to said distal end of said supply tube, said low pressure passageway having at least one distal port and at least one proximal port, said at least one proximal port of said low pressure passageway being connected with a lumen of said return tubes, said high pressure passageway and said low pressure passageway each following a respective tortuous flow path with a substantial portion of each said flow path being transverse to a longitudinal axis of said heat exchanger, to create turbulent flow;

a Joule-Thomson expansion element mounted within said return tube, said expansion element being connected to said distal port of said high pressure passageway of said heat exchanger for isenthalpically expanding said gas mixture from said higher pressure to a lower pressure, said expanded gas mixture thereby cooling to a temperature of no greater than 183K, said expanded gas mixture being in fluid flow communication with said at least one distal port of said low pressure passageway; and a heat transfer body mounted to said distal end of said return tube adjacent said expansion element, said body having an inner surface exposed to said expanded gas mixture and an outer surface exposed to ambient, for transferring heat from said outer surface of said body to said inner surface of said body.

2. A miniature refrigeration system, comprising:

a compressor for pressurizing a gas mixture to a pressure of approximately 420 psia, said compressor having an inlet and an outlet;

a hollow elongated supply tube, said supply tube having a proximal end and a distal end, said proximal end of said supply tube being connectable to said outlet of said compressor;

a hollow elongated return tube disposable substantially coaxially over said supply tube, said return tube having a proximal end and a distal end, said proximal end of said return tube being connectable to said inlet of said compressor;

a laminated counterflow heat exchanger mounted within said return tube, adjacent to said distal end of said return tube, said heat exchanger having a high pressure passageway and a low pressure passageway, said high pressure passageway having at least one proximal port and at least one distal port, said at least one proximal port of said high pressure passageway being connected to said distal end of said supply tube, said low pressure passageway having at least one distal port and at least one proximal port, said at least one proximal port of said low pressure passageway being connected with a lumen of said return tube;

a Joule-Thomson expansion element mounted within said return tube, said expansion element being connected to said distal port of said high pressure passageway of said heat exchanger for isenthalpically expanding said gas mixture from said higher pressure to a lower pressure, said expanded gas mixture thereby cooling to a temperature of no greater than 183K, said expanded gas mixture being in fluid flow communication with said at least one distal port of said low pressure passageway; and a heat transfer body mounted to said distal end of said return tube adjacent said expansion element, said body having an inner surface exposed to said expanded gas mixture and an outer surface exposed to ambient, for transferring heat from said outer surface of said body to said inner surface of said body;

wherein said expansion element comprises:

a substantially cylindrical metallic container open at both ends; and a plurality of microscopic metallic beads sintered into the interior of said metallic container to form a permeable flow impedance.

3. A miniature refrigeration system, comprising:

a compressor for pressurizing a gas mixture to a pressure of approximately 420 psia, said compressor having an inlet and an outlet;

a hollow elongated supply tube, said supply tube having a proximal end and a distal end, said proximal end of said supply tube being connectable to said outlet of said compressor;

a hollow elongated return tube disposable substantially coaxially over said supply tube, said return tube having a proximal end and a distal end, said proximal end of said return tube being connectable to said inlet of said compressor;

a laminated counterflow heat exchanger mounted within said return tube, adjacent to said distal end of said return tube, said heat exchanger having a high pressure passageway and a low pressure passageway, said high pressure passageway having at least one proximal port and at least one distal port, said at least one proximal port of said high pressure passageway being connected to said distal end of said supply tube, said low pressure passageway having at least one distal port and at least one proximal port, said at least one proximal port of said low pressure passageway being connected with a lumen of said return tube;

a Joule-Thomson expansion element mounted within said return tube, said expansion element being connected to said distal port of said high pressure passageway of said heat exchanger for isenthalpically expanding said gas mixture from said higher pressure to a lower pressure, said expanded gas mixture thereby cooling to a temperature of no greater than 183K, said expanded gas mixture being in fluid flow communication with said at least one distal port of said low pressure passageway; and a heat transfer body mounted to said distal end of said return tube adjacent said expansion element, said body having an inner surface exposed to said expanded gas mixture and an outer surface exposed to ambient, for transferring heat from said outer surface of said body to said inner surface of said body;

wherein said expansion element comprises:

a first substantially cylindrical metallic container having a first diameter, said first container being open at both ends;

a first plurality of microscopic metallic beads sintered into the interior of said first container to form a first permeable flow impedance, said first plurality of beads being sized to expand said gas mixture isenthalpically;

a second substantially cylindrical metallic container having a second diameter greater than said first diameter, said second container being open at both ends; and a second plurality of microscopic metallic beads sintered into the interior of said second container to form a second permeable flow impedance, said second plurality of metallic beads being sized to expand said gas mixture isothermally.

4. A miniature refrigeration system, comprising:

a compressor for pressurizing a gas mixture to a pressure of approximately 420 psia, said compressor having an inlet and an outlet;

a hollow elongated supply tube, said supply tube having a proximal end and a distal end, said proximal end of said supply tube being connectable to said outlet of said compressor;

a hollow elongated return tube disposable substantially coaxially over said supply tube, said return tube having a proximal end and a distal end, said proximal end of said return tube being connectable to said inlet of said compressor;

a laminated counterflow heat exchanger mounted within said return tube, adjacent to said distal end of said return tube, said heat exchanger having a high pressure passageway and a low pressure passageway, said high pressure passageway having at least one proximal port and at least one distal port, said at least one proximal port of said high pressure passageway being connected to said distal end of said supply tube, said low pressure passageway having at least one distal port and at least one proximal port, said at least one proximal port of said low pressure passageway being connected with a lumen of said return tube;

a Joule-Thomson expansion element mounted within said return tube, said expansion element being connected to said distal port of said high pressure passageway of said heat exchanger for isenthalpically expanding said gas mixture from said higher pressure to a lower pressure, said expanded gas mixture thereby cooling to a temperature of no greater than 183K, said expanded gas mixture being in fluid flow communication with said at least one distal port of said low pressure passageway; and a heat transfer body mounted to said distal end of said return tube adjacent said expansion element, said body having an inner surface exposed to said expanded gas mixture and an outer surface exposed to ambient, for transferring heat from said outer surface of said body to said inner surface of said body;

wherein said heat exchanger comprises a plurality of laminated members, said laminated members being constructed and arranged to establish said high pressure passageway and said low pressure passageway; and wherein said laminated members comprise:

a plurality of flat plates and a plurality of flat spacers stacked axially along said heat exchanger, said plates being alternated with said spacers;

a first plurality of openings formed through said plates and said spacers to establish said high pressure passageway, with said proximal high pressure port at a proximal end of said stack and said distal high pressure port at a distal end of said stack, said first plurality of openings in each said plate being transversely offset from said first plurality of openings in adjacent said plates, to create a tortuous high pressure flow path with a substantial portion of said high pressure flow path being transverse to a longitudinal axis of said heat exchanger to create turbulent high pressure flow; and a second plurality of openings formed through said plates and said spacers to establish said low pressure passageway, with said proximal low pressure port at said proximal end of said stack and said distal low pressure port at said distal end of said stack, said second plurality of openings in each said plate being transversely offset from said second plurality of openings in adjacent said plates, to create a tortuous low pressure flow path with a substantial portion of said low pressure flow path being transverse to a longitudinal axis of said heat exchanger to create turbulent low pressure flow.

5. A miniature refrigeration system, comprising;

a compressor for pressurizing a gas mixture to a pressure of approximately 420 psia, said compressor having an inlet and an outlet;

a hollow elongated supply tube, said supply tube having a proximal end and a distal end, said proximal end of said supply tube being connectable to said outlet of said compressor;

a hollow elongated return tube disposable substantially coaxially over said supply tube, said return tube having a proximal end and a distal end, said proximal end of said return tube being connectable to said inlet of said compressor;

a laminated counterflow heat exchanger mounted within said return tube, adjacent to said distal end of said return tube, said heat exchanger having a high pressure passageway and a low pressure passageway, said high pressure passageway having at least one proximal port and at least one distal port said at least one proximal port of said high pressure passageway being connected to said distal end of said supply tube, said low pressure passageway having at least one distal port and at least one proximal port, said at least one proximal port of said low pressure passageway being connected with a lumen of said return tube;

a Joule-Thomson expansion element mounted within said return tube, said expansion element being connected to said distal port of said high pressure passageway of said heat exchanger for isenthalpically expanding said gas mixture from said higher pressure to a lower pressure said expanded gas mixture thereby cooling to a temperature of no greater than 183K, said expanded gas mixture being in fluid flow communication with said at least one distal port of said low pressure passageway; and a heat transfer body mounted to said distal end of said return tube adjacent said expansion element, said body having an inner surface exposed to said expanded gas mixture and an outer surface exposed to ambient, for transferring heat from said outer surface of said body to said inner surface of said body;

wherein said heat exchanger comprises a plurality of laminated members, said laminated members being constructed and arranged to establish said high pressure passageway and said low pressure passageway; and wherein said laminated members comprise:
 a first sheet having a first flow channel etched therein to form said high pressure passageway, with said proximal high pressure port at a proximal edge of said first sheet and said distal high pressure port at a distal edge of said first sheet; and
 a second sheet having a second flow channel etched therein to form said low pressure passageway, with said proximal low pressure port at a proximal edge of said second sheet and said distal low pressure port at a distal edge of said second sheet;
 wherein said first and second sheets are rolled into a cylindrical shape having said proximal ports at a proximal end and said distal ports at a distal end.

6. A miniature refrigeration system, comprising:

a compressor for pressurizing a gas mixture to a pressure of approximately 420 psia, said compressor having an inlet and an outlet;

a hollow elongated gas mixture supply tube, said supply tube having a proximal end and a distal end, said proximal end of said supply tube being connectable to said outlet of said compressor;

a hollow elongated gas mixture return tube disposable substantially coaxially over said supply tube, said return tube having a proximal end and a distal end, said proximal end of said return tube being connectable to said inlet of said compressor;

a substantially cylindrical counterflow heat exchanger mounted within said return tube, adjacent to said distal end of said return tube, said heat exchanger comprising a plurality of laminated members, each of said laminated members having a first plurality of openings transversely offset from openings in adjacent said laminated members, establishing a first tortuous path for said supply gas mixture with a substantial portion of said first tortuous path being transverse to a longitudinal axis of said heat exchanger to create turbulent high pressure flow, and each of said laminated members having a second plurality of openings transversely offset from openings in adjacent said laminated members, establishing a second tortuous path for said return gas mixture with a substantial portion of said second tortuous path being transverse to a longitudinal axis of said heat exchanger to create turbulent low pressure flow, said supply path having at least one proximal port and at least one distal port, said at least one proximal port of said supply path being connected to said distal end of said supply tube, said return path having at least one distal port and at least one proximal port, said at least one proximal port of said return path being connected with a lumen of said return tube;

a Joule-Thomson two stage expansion element mountable within said return tube, said expansion element having an inlet connected to said distal port of said supply path of said heat exchanger, said expansion element having an outlet for releasing said gas mixture to enter said distal port of said return path of said heat exchanger adjacent said distal end of said return tube;

a first, isenthalpic, expansion stage in said expansion element for expanding said gas mixture from said supply pressure to a lower pressure, said expanded gas mixture thereby cooling to a temperature of no greater than 183K to allow said expanded gas mixture to absorb heat from surrounding components;

a second, isothermal, expansion stage in said expansion element, downstream of said first stage, for further expanding said gas mixture to absorb additional heat from surrounding components; and a metallic heat transfer element sealingly mounted through an aperture in a wall of said return tube adjacent said expansion element, said heat transfer element having an inner surface exposed to said twice expanded gas mixture and an outer surface exposed to ambient, for transferring heat from ambient to said gas mixture.

7. A method for cooling a remote body, comprising the steps of:

providing a gas mixture capable of isenthalpically expanding to a temperature below 183K from a pressure of no more than 420 psia;

providing a miniature refrigeration system having a compressor for pressurizing said gas mixture to a pressure of no more than 420 psia, a supply tube having an inlet end connected to an outlet of said compressor, and a return tube disposed coaxially over said supply tube and having an outlet connected to an inlet of said compressor;

providing a laminate construction counterflow heat exchanger within a distal section of said return tube, said heat exchanger having a high pressure section and a low pressure section, said high pressure section having an inlet connected to an outlet of said supply tube and said low pressure section having an outlet connected to an inlet of said return tube said high pressure section and said low pressure section each following a respective tortuous flow path with a substantial portion of each said flow path being transverse to a longitudinal axis of said heat exchanger, to create turbulent flow;

providing a two stage Joule-Thomson expansion element having an inlet connected to an outlet of said high pressure section of said heat exchanger and having an outlet adjacent to a metallic heat transfer element and adjacent to an inlet of said low pressure section of said heat exchanger;

placing said heat transfer element in contact with said remote body to be cooled;

compressing said gas mixture to no more than 420 psia;

conducting said compressed gas mixture to said high pressure inlet of said heat exchanger via said supply tube;

precooling said compressed gas mixture via turbulent gas flow in said high pressure section of said heat exchanger by transferring heat to turbulent gas flow in said low pressure section of said heat exchanger;

isenthalpically expanding said gas mixture in a first stage of said expansion element to cool said gas mixture to below 183K, allowing said expanded gas mixture to absorb heat from surrounding components;

isothermally expanding said gas mixture in a second stage of said expansion element, allowing said further expanded gas mixture to absorb additional heat from surrounding components;

absorbing heat from said heat transfer element by contact with said further expanded gas mixture, to cool said heat transfer element to below 180K; and absorbing heat from said item to be cooled, by contact with said heat transfer element.

\* \* \* \* \*